US012714685B2

(12) United States Patent
Panotopoulos

(10) Patent No.: US 12,714,685 B2
(45) Date of Patent: Aug. 25, 2026

(54) DRUG COMBINATION AND ITS USE IN THE TREATMENT OF CANCER

(71) Applicant: Inderes LTD, Limassol (CY)

(72) Inventor: Christos Panotopoulos, Limassol (CY)

(73) Assignee: Inderes LTD, Limassol (CY)

( * ) Notice: Subject to any disclaimer, the term of this patent is extended or adjusted under 35 U.S.C. 154(b) by 679 days.

(21) Appl. No.: 18/019,454

(22) PCT Filed: Jul. 26, 2021

(86) PCT No.: PCT/IB2021/056735
§ 371 (c)(1),
(2) Date: Feb. 2, 2023

(87) PCT Pub. No.: WO2022/029555
PCT Pub. Date: Feb. 10, 2022

(65) Prior Publication Data

US 2023/0277488 A1 Sep. 7, 2023

(30) Foreign Application Priority Data

Aug. 3, 2020 (GR) .............................. 20200100456

(51) Int. Cl.

| | |
|---|---|
| ***A61K 31/197*** | (2006.01) |
| ***A61K 31/517*** | (2006.01) |
| ***A61K 45/06*** | (2006.01) |
| ***A61P 35/00*** | (2006.01) |

(52) U.S. Cl.
CPC .......... *A61K 31/197* (2013.01); *A61K 31/517* (2013.01); *A61K 45/06* (2013.01); *A61P 35/00* (2018.01)

(58) Field of Classification Search
CPC .... A61K 31/197; A61K 31/517; A61K 45/06; A61P 35/00
See application file for complete search history.

(56) References Cited

FOREIGN PATENT DOCUMENTS

EP 0 799 618 A2 10/1997

OTHER PUBLICATIONS

Liu et al. (Cellular & Molecular Immunology. 2024;21:1354-1375) (Year: 2024).*
Fan et al. (PLOS ONE.2014;9(4):1-14). (Year: 2014).*
Jones et al. (Biochemical and Biophysical Research Communications. 1994;205(3):1681-1687). (Year: 1994).*
An, Ming et al.; "Prazosin inhibits the growth and mobility of osteosarcoma cells" Transl Cancer Res 2019; 8(5):1997-2004; doi: 10.21037/ter.2019.09.03.
Azzarito, T. et al.; "Lansoprazole induces sensitivity to suboptimal doses of paclitaxel in human melanoma" Cancer Letters, vol. 356, Issue 2, Part B, 2015, pp. 697-703, ISSN 0304-3835, https://doi.org/10.1016/j.canlet.2014.10.017.
Basso, J. et al.; "Repurposing drugs for glioblastoma: From bench to bedside" Cancer Letters, vol. 428, 2018, pp. 173-183, ISSN 0304-3835, https://doi.org/10.1016/j.canlet.2018.04.039.
Batty, Mallory et al.; "The Role of α1-Adrenoceptor Antagonists in the Treatment of Prostate and Other Cancers" Int. J. Mol. Sci.; 2016; 17, 1339; 25 pages; doi:10.3390/ijms17081339.
Bergenheim, A. Tommy et al.; "Metabolic manipulation of glioblastoma in vivo by retrograde microdialysis of L-2, 4 diaminobutyric acid (DAB)" J Neurooncol (2006); 80:285-293; DOI 10.1007/s11060-006-9186-1.
Blind, Per-Jonas et al.; "Antitumour Effect of L-2,4 Diaminobutyric Acid on a Hepatoma Cell Line" Anticancer Research (2000); 20:4275-4278.
Blind, Per-Jonas et al.; "Unique Antitumour Effect of L-2,4 Diaminobutyric Acid on Cultured Hepatoma Cells" Anticancer Research (2003); 23:1245-1248.
Calcinotto, Arianna et al.; "Modulation of Microenvironment Acidity Reverses Anergy in Human and Murine Tumor-Infiltrating T Lymphocytes" American Association for Cancer Research; 72(11); Jun. 1, 2012; pp. 2746-2756; DOI: 10.1158/0008-5472.CAN-11-1272.
Cavero, I. et al.; "The pharmacology of prazosin, a novel antihypertensive agent" Life Sciences; vol. 27, Issue 17, 1980, pp. 1525-1540, ISSN 0024-3205, https://doi.org/10.1016/0024-3205(80)90561-5.
Christensen, Halvor N. et al.; "Energization of Amino Acid Transport, Studied for the Ehrlich Ascites Tumor Cell" Biochimica et Biophysica Acta; 300 (1973) pp. 487-522.
Christensen, Halvor N. et al.; "Membrane Transport Properties of L-2,4 Diaminobutyrate Revisited" J Membr Biol. Apr. 1992; 127(1):1-7. doi: 10.1007/BF00232753. PMID: 1404338.
Christensen, Halvor N. et al.; "Modified Transport Substrates as Probes for Intramembrane Gradients" Annals New York Academy of Sciences; Feb. 18, 1974;227:355-79. doi: 10.1111/j.1749-6632.1974.tb14400.x. PMID: 4133305.
Coelho, Barbara Paranhos et al.; "Dual Effect of Doxazosin: Anticancer Activity on SH-SY5Y Neuroblastoma Cells and Neuroprotection on an In Vitro Model of Alzheimer's Disease" Nueroscience 404 (Feb. 14, 2019) pp. 314-325; https://doi.org/10.1016/j.neuroscience.2019.02.005.
https://radiopaedia.org/articles/rano-criteria-for-glioblastoma; accessed Feb. 6, 2023.
Kahn, Suzana Assad et al.; "The anti-hypertensive drug prazosin inhibits glioblastoma growth via the PKCd-dependent inhibition of the AKT pathway" EMBO Molecular Medicine; 2016; 16 pages; DOI 10.15252/emmm.201505421.

(Continued)

*Primary Examiner* — Clinton A Brooks
*Assistant Examiner* — Jerica Katlynn Wilson
(74) *Attorney, Agent, or Firm* — Thorpe North & Western, LLP.; David W. Osborne

(57) ABSTRACT

The present invention discloses a pharmaceutical product comprising L-2,4-diaminobutyric acid (DAB) and prazosin for use in the treatment of cancer by administration to the tumor. The invention also discloses the use of the said at least two active agents in the manufacture of a medicament and methods for the treatment of a cancer comprising intratumoral administration of the pharmaceutical formulation using a novel way of delivery.

9 Claims, 4 Drawing Sheets

(56) References Cited

OTHER PUBLICATIONS

Lyne, Sean B. et al; "An Alternative Pipeline for Glioblastoma Therapeutics: A Systemic Review of Drug Repurposing in Glioblastoma" Cancers 2021, 13, 1953 (29 pages); https://doi.org/10.3390/cancers13081953.

Orahoske, Cody M.; "Dimeric small molecule agonists of EphA2 receptor inhibit glioblastoma cell growth" Bioorg med Chem; Sep. 15, 2020; 28(18): 115656; 27 pages; doi: 10.1016/j.bmc.2020.115656.

Panasci, L. et al.; "The cytolytic effect of L-2,4 diaminobutyric acid with malignant glioma cells and fibroblasts" Cancer Chemother. Pharmacol. 21, 143-144 (1988).

Ronquist, G. et al. "Antitumor activity of L-2,4 diaminobuturic acid against mouse fibrosarcoma cells in vitro and in vivo" J Cancer Res Clin Oncol 96, 259-268 (1980). https://doi.org/10.1007/BF00408098.

Ronquist, G. et al.; Induction of complete and irreversible damage to malignant glioma cells by L-2,4 diaminobutyric acid Anticancer Res. Jul.-Oct. 1984;4(4-5):225-228; PMID: 6486725; https://pubmed.ncbi.nlm.nih.gov/6486725/.

Ronquist, G. et al.; "Treatment of Malignant Glioma by a New Therapeutic Principle" Acta Neurochir (Wien); 1992; 114: 8-11.

Ronquist, G., et al.; "α-Aminoisobutyric Acid Transport into Human Glia and Glioma Cells in Culture" J. Cell. Physiol., 1976; 89: 433-439. https://doi.org/10.1002/jcp.1040890309.

Sjölander, U et al.; "Naloxone as an adjuvant in chemotherapy of an experimental tumor" J Cancer Res Clin Oncol 108, 246-248 (1984). https://doi.org/10.1007/BF00402477.

Sun, Xiaogang et al.; "Prazosin inhibits the proliferation and survival of acute myeloid leukaemia cells through down-regulating TNS1" Biomedicine & Pharmacotherapy 124 (2020) 109731; 8 pages; https://doi.org/10.1016/j.biopha.2019.109731.

Zhang, J. et al.; "Prazosin inhibits the proliferation, migration and invasion, but promotes the apoptosis of U251 and U87 cells via the PI3K/AKT/mTOR signaling pathway" Experimental and Therapeutic Medicine 20, No. 2 (2020): 1145-1152; https://doi.org/10.3892/etm.2020.8772.

* cited by examiner

DRUG COMBINATION AND ITS USE IN THE TREATMENT OF CANCER

PRIORITY DATA

This application is a 371 U.S. national stage entry of PCT Application Serial No. PCT/IB2021/056735, filed Jul. 26, 2021, which claims priority to Greece Patent Application Serial No. 20200100456, filed on Aug. 3, 2020, each of which are incorporated herein by reference.

FIELD OF THE INVENTION

The present invention relates to a drug combination, its compositions and its use in the treatment of cancer, in particular when delivered in a novel way.

BACKGROUND

Cancer is a disease in which a group of cells display the traits of uncontrolled growth. This means that the cells grow and divide beyond the levels of normal limits. The uncontrolled division (mitosis) of cancer cells implies the supply of physiological amino acids that are the building stones of proteins, i.e. were it not for those, a cell division (mitosis) would not be feasible. The cells are also able to invade and destroy surrounding tissues. In addition, cancer cells sometimes also metastasize, meaning that they spread to other locations in the body via the blood or lymph.

Most cancers are caused by abnormalities in the genetic material of the cells. These abnormalities may be due to the effects of carcinogens. Other cancer-promoting genetic abnormalities may be randomly acquired through epigenetic factors or errors in DNA replication, or are inherited, and thus present in cells from birth.

Genetic abnormalities found in cancer typically affect two general classes of genes. Cancer-promoting oncogenes are often activated in cancer cells, giving those cells new properties, such as hyperactive growth and division, protection against programmed cell death, loss of respect for normal tissue boundaries, and the ability to become established and grow in diverse tissue environments.

Tumor suppressor genes are often inactivated in cancer cells, resulting in the loss of normal functions in those cells, such as accurate DNA replication, control over the cell cycle, orientation and adhesion within tissues, and interaction with protective cells of the immune system.

There are many different types of cancer and the cancer is usually classified according to the type of tissue from which it originated.

Cancer is usually treated by one or more of the following: surgery, chemotherapy, radiation therapy, immunotherapy including monoclonal antibody therapy. The type of therapy depends upon the location and grade of the tumor and the stage of the disease.

Complete removal of the cancer without damage to the rest of the body is the goal of treatment. Sometimes this can be accomplished by surgery, but the propensity of cancers to invade adjacent tissue or to spread to distant sites by microscopic metastasis often limits its effectiveness. The effectiveness of chemotherapy is often limited by different modes of cancer cells to evade its working principle and by toxicity to other tissues in the body. Radiation can also cause damage to normal tissue.

Cancers are known to affect many areas of the body with the most common types of cancers including, in the order of incidence (Source: Estimated new cases 2018 by cancer type (both sexes combined) American Cancer Society https://cancerstatisticscenter.cancer.org/#!/): cancer of the breast; cancer of the lung, cancer of the prostate, cancer of colon melanoma, cancer of urinary bladder, non-Hodgkin's lymphoma, cancer of the kidney, cancer of the uterus, leukemia, cancer of the pancreas, cancer of the thyroid, cancer of the oral cavity and pharynx, cancer of the liver, multiple myeloma, cancer of the stomach, cancer of the brain, spinal cord and other nervous system, cancer of the ovaries, cancer of the esophagus, cancer of the cervix, cancer of the larynx, cancer of soft tissue (including heart), cancer of gall bladder and other biliary (bile duct etc.), cancer of small intestine, testicular cancer, cancer of anus, anal canal and anorectum, Hodgkin's lymphoma, cancer of the vulva, cancer of the vagina, ureter and other urinary organs, cancer of the eye and orbit, cancer of the bone, and cancer of the penis, and also the following (no ranking according incidence): neuroendocrine tumors (including carcinoids and other types), cancer of the head and neck, Kaposi's sarcoma, cancer of the lymph nodes, mesothelioma, skin cancer, soft tissue sarcomas, adrenal cancer, rhabdomyosarcoma, salivary gland cancer, and thymus cancer.

A tumor that develops in the brain can destroy or damage brain cells by producing inflammation, compressing other parts of the brain, inducing cerebral oedema (brain swelling) and can cause increases in intracranial pressure (pressure within the skull).

Each year, approximately 4300 people in the UK are diagnosed with a brain tumor. A primary brain tumor is a mass created by the growth or uncontrolled proliferation of cells in the brain. Malignant primary brain tumors are most likely to cause problems by spreading into the normal brain tissue which surrounds them and causing pressure and damage to the surrounding areas of the brain. These tumors rarely spread outside the brain to other parts of the body. However, secondary brain tumors occur when cancer cells from other parts of the body, such as the lung or breast spread to the brain.

Surgery is the treatment option of choice for many brain tumors. Some may be completely excised, but those that are deep or that infiltrate brain tissue may be debulked rather than removed.

Radiation therapy and chemotherapy may be recommended depending on the type of tumor involved.

Glioma cell tumors often have a poor prognosis. The characteristic diffuse infiltrative tumor growth of gliomas often makes the surgical removal of them impossible and this profoundly complicates the clinical management of these patients.

Glioblastoma multiforme (GBM) is the most common and most aggressive type of primary brain tumor and accounts for 52% of all primary brain tumor cases and 20% of all intracranial tumors. The average survival time is 12-18 months with only 25% of glioblastoma patients surviving more than one year and only 5% of patients more than five years.

Different approaches are being researched to improve the mortality rate of patients diagnosed with a glioma. These include therapies that target the glioma cells but leave normal cells unharmed, methods that limit the spread of the cancer cells and treatments that block the tumors life-sustaining molecules.

However, despite all the efforts for developing cancer treatments, there is still the need of providing new approaches for the management of cancer, in particular of brain tumors.

More particularly, there is still a need for new efficient and less toxic approaches for the treatment of cancer.

L-2,4 diaminobutyric acid (DAB) is a synthetic (non-physiological) cationic amino acid analogue which has shown antitumoral activity in vitro against human glioma cells (Ronquist G et al., Anticancer Res 4 (1984) 225-228; Panasci L et al., Cancer Chemother Pharmacol 21 (1988) 143-144). The clinical use of L-2,4 diaminobutyric acid (DAB) has been however restricted to a small patient series (Ronquist et al., (1992) Acta Neurochirurgica 114, 8-11; Bergenheim et al., (2006) Journal of Neuro-Oncology 80, 285-293). The two clinical studies have failed to demonstrate significant clinical benefit.

Prazosin is a clinically approved drug and has been adopted for more than 40 years in clinical practice to treat hypertension (Cavero & Roach, 1980). Its use has been extended to treat benign prostatic hyperplasia, congestive heart failure, pheochromocytoma, sleep problems associated with post-traumatic stress disorder and Raynaud's disease. For the treatment of hypertension, prazosin hydrochloride is used as an oral prescription with a recommended total daily dose of 20 to 40 mg given in divided doses. Although it has been reported to inhibit glioblastoma growth in mouse xenografts (Assad Kahn et al., 2016, EMBO Mol. Med. 8, 511-526), there is no report of any clinical use of prazosin as an anticancer agent.

SUMMARY OF THE INVENTION

The present disclosure provides drug combinations, pharmaceutical products and methods for the treatment of cancer which overcome at least part of the problems outlined above. The combinations of the invention are effective in inhibiting the development of tumors, in particular brain tumors in humans.

The present invention is based at least in part on data showing a synergistic cytotoxic effect for L-2,4 diaminobutyric acid (DAB) combined with prazosin against human glioma cell lines. Furthermore, the cytotoxicity is selective towards malignant cells versus non-malignant cells.

According to a first aspect, the present invention is a product comprising at least L-2,4diaminobutyric acid (DAB) and prazosin, as a combined preparation for separate, simultaneous or sequential use in the treatment or prevention of cancer.

According to a second aspect, the present invention is a composition comprising at least L-2,4diaminobutyric acid (DAB) and prazosin for use in the treatment or prevention of cancer.

The drug combinations of the invention are effective in inhibiting the development of tumors, in particular in reducing the growth of brain tumors in a subject and limiting the spread of the cancer cells. Advantageously, the combinations of the invention target the brain tumor cells but leave normal cells unharmed. This is particularly important in the brain. The combination of the two active agents according to the invention may have one or more of the following advantageous properties: exhibits reduced adverse side effects; stability in aqueous environments; selectively cytotoxic to cancer cells; and exhibits reduced cytotoxicity to non-malignant cells. In addition, the product may further comprise an additional therapeutic agent or may be administered to subjects with an additional therapeutic agent.

The present disclosure provides thus a product comprising the active agents L-2,4-diaminobutyric acid (DAB) and prazosin for use in the treatment of cancer by intratumoral administration to the tumor. The intratumoral administration of the combination permits active drug concentrations at the tumor that are not possible with systemic administration. The intratumoral administration also results in less adverse side effects due to systemic exposure to the active agents. Furthermore, the use of the combination of the invention can result in less side effects than treatment with other anticancer drugs. Common adverse effects of chemotherapeutic agents include: fatigue, hair loss, easy bruising and bleeding, infection, anemia (low red blood cell counts), nausea and vomiting, appetite changes, constipation, diarrhea, mouth, tongue, and throat problems such as sores and pain with swallowing, peripheral neuropathy or other nerve problems, such as numbness, tingling, and pain, skin and nail changes such as dry skin and color change, urine and bladder changes and kidney problems, weight changes, chemo brain, which can affect concentration and focus, mood changes, changes in libido and sexual function, fertility problems.

The present disclosure provides thus a product comprising the active agents L-2,4-diaminobutyric acid (DAB) and prazosin for use in the treatment of cancer by intratumoral administration to the tumor.

The cancer to be treated may be any cancerous or malignant tumor. The malignant tumor may be a tumor in the central nervous system or anywhere in the body suitable for intratumoral administration. Preferably the cancer to be treated is a brain tumor.

Brain tumors are usually classified according to the location of the tumor and the type of cell that the cancer has developed from. For example, different types of brain tumor include: acoustic neuroma, astrocytoma, CNS lymphoma, ependymoma, haemangioblastoma, medulloblastoma, meningioma, glioma, mixed glioma, oligodendroglioma, pineal region tumors and pituitary tumors. Gliomas are tumors of the glial cells; these cells support and protect nerve cells in the brain. Gliomas comprise nearly half of all primary brain tumors and a fifth of all primary spinal cord tumors.

The disclosure further provides the use of a combination of at least L-2,4-diaminobutyric acid (DAB) and prazosin in the manufacture of a medicament for the treatment of a cancer for intratumoral administration.

According to another aspect, the combination for use according to the invention is administered intratumorally using a novel drug delivery method. This novel drug delivery method results in an enhancement of the therapeutic action of the combination.

In one aspect, the method involves infusion of the combination of the invention through one or more catheters left inside the tumor, the tumor's resection cavity or biopsy site, with periodical interruptions for drainage and infusion.

Typically, the method involves infusion of the combination of the invention through one or more catheters left inside the tumor, the tumor's resection cavity or a biopsy site, with a specified flow rate (e.g. with a total flow rate of ~3 ml/hour), with periodical interruptions for drainage and infusion of a physiological isotonic fluid and/or of an isotonic Tris buffer. Preferably the buffer has a pH of 7.2-9.1. Preferably the volume of infusion of isotonic fluid is 1-2 ml. In a preferred embodiment, the volume of infusion of isotonic fluid is equal or less to the drained fluid volume. Preferably the above interruptions include passive drainage or manual aspirations of 1-2 ml through a syringe for a few seconds, followed by 1-2 ml infusions, alternatively, for a time period, for example a 5 minute period. In another preferred method, an Irraflow, or any other fluid exchange catheter or combination of catheters, can exchange the intratumoral fluid environment as above, if left in place post operatively and activated periodically (like every two hours)

for ~5 minutes. In an additional preferred method for inoperable cases or patients programmed only for biopsy, multiple infusion and fluid exchange catheters can be inserted through a cranioanatresis and create optimal drug and buffer distribution, when placed and programmed to function at different tumor parts.

The present disclosure still further provides a method for the treatment of a cancer which comprises the intratumoral administration of the product described herein comprising L-2,4-diaminobutyric acid (DAB) and prazosin to a subject in need thereof. The said products are administered directly into a tumor, i.e., intratumorally, by a novel drug delivery method comprising infusion of the combination through one or more catheters left inside a tumor, the tumor's resection cavity, or biopsy site (preferably at a total flow rate of approximately 3 ml/hour), with periodical interruptions for drainage and infusion of preferably 1-2 ml of isotonic Tris buffer, pH7.2-9.1 as described in the above paragraph.

This periodical evacuation of the surgical wound's extracellular fluid and infusion of isotonic Tris buffer, pH 7.2-9.1, results in an enhanced therapeutic effect.

Without being bound by theory, it is believed that administration of the combination of DAB and Prazosin intratumorally using this delivery method, results in an increase of the drugs-target cells interaction. Thus, it is envisioned that the method increases the interaction of active drug molecules with malignant cells by evacuating competing physiological amino acids (see below), inactive drug metabolites and cellular debris of previous treatment, now acting as a protective shield for malignant cells—not allowing new drug penetration.

Additionally, DAB's action may be enhanced when its competing extracellular amino-acids' concentrations are lowered by the periodical "washing" of the wound, while DAB's and Prazosin's penetration to the peritumoral tissue zone, where the glioma initiating cells-responsible for tumor recurrence reside, may be enhanced by the diffusion and convection forces created during the periodical drainage-infusions of drugs, buffers and physiologic fluids. This mode of administration of active drugs in a Tris-buffered solution, pH 7.2-9.1, in concert with intermediate, preferably slightly alkaline, washings with the buffer, may create a changed microenvironment of the cancer, resulting in an enhanced effect of the active agents. It is well known that low extracellular pH in tumor microenvironment has been correlated with better survival and immune escape by the cancer (Calcinotto A et al., Cancer Res 72 (2012) 2746-2756; Azzarito T et al., Cancer Lett 356 (2015) 697-703). The acidic condition also increases the release of so called "exosomes" from the tumor cells that in a paracrine way enhance the tumor proliferation.

Various intratumoral methods of drug administration have been described for the treatment of gliomas. All the methods described for these experimental treatments, however, involve continuous or intermittent drug infusions but not periodically alternated with drainage or infusion of physiologic fluids, and/or, slightly alkaline Tris-buffered solution like the method of the invention.

The method of treatment can also comprise the administration of an additional therapeutic agent.

Although, the preferred subject is a human, the present invention has application in the veterinary and animal husbandry industries and hence extends to non-human animals.

DETAILED DESCRIPTION OF THE INVENTION

Figure 1:
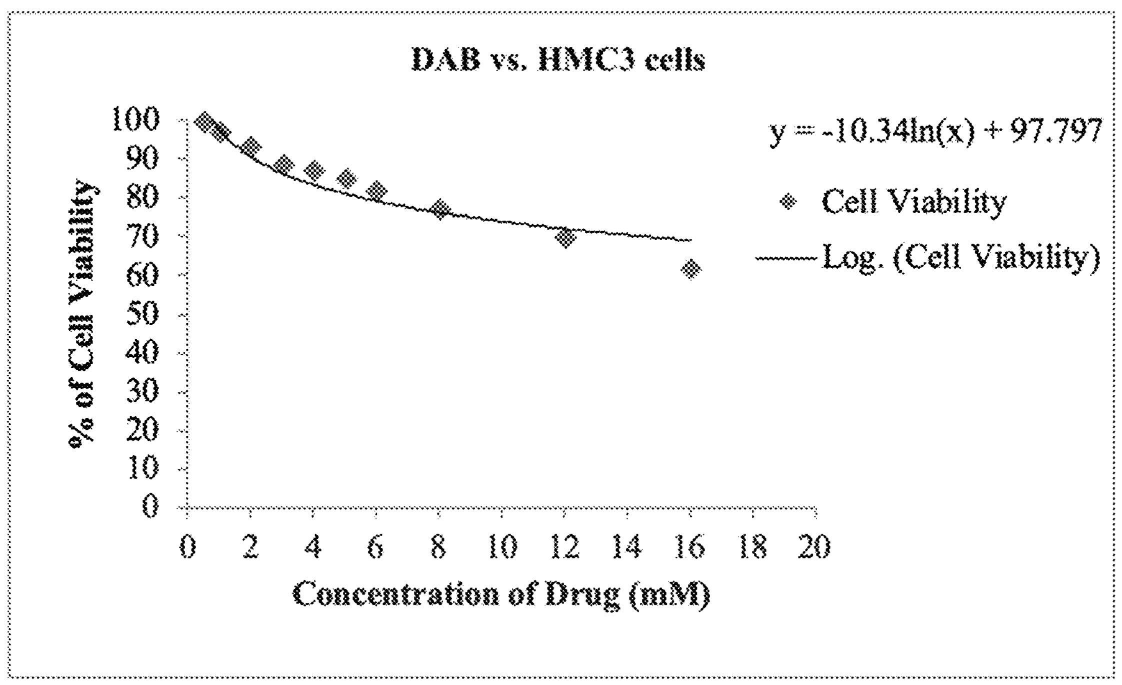
FIG. 1 shows a dose-response effect of DAB on viability of cultured HMC3 cells.

A pharmaceutical product comprising L-2,4-diaminobutyric acid (DAB) and prazosin, as a combined preparation for separate, simultaneous, or sequential use, is used in the treatment of a cancer by intratumoral administration.

In the context of the present invention, and unless otherwise specifically stated, the term "treatment" may refer to the cure or the amelioration of the cancer condition, i.e. to the complete elimination or reduction of the recurrence of cancer, including the delay in the recurrence of cancer (progression free interval, PFS), to the complete elimination of a tumor, to the inhibition of tumor growth, to an increase in survival time or better quality of life of the patient.

The cancer to be treated may be, for example, a cancer of the bile duct, cancer of the bladder, cancer of the bone, cancer of the bowel (including cancer of the colon and cancer of the rectum), cancer of the brain, cancer of the breast, cancer of the neuroendocrine system (commonly known as a carcinoid), cancer of the cervix, cancer of the eye, cancer of the oesophagus, cancer of the head and neck (this group includes carcinomas that start in the cells that form the lining of the mouth, nose, throat, ear or the surface layer covering the tongue), Kaposi's sarcoma, cancer of the kidney, cancer of the larynx, leukaemia, cancer of the liver, cancer of the lung, cancer of the lymph nodes, Hodgkin's lymphoma, non-Hodgkin's lymphoma, melanoma, mesothelioma, myeloma, cancer of the ovary, cancer of the pancreas, cancer of the penis, cancer of the prostate, skin cancer, soft tissue sarcomas, cancer of the spinal cord, cancer of the stomach, testicular cancer, cancer of the thyroid, cancer of the vagina, cancer of the vulva and cancer of the uterus.

In some particular embodiments the cancer to be treated is a brain tumor.

Brain tumors include: acoustic neuroma, astrocytoma, CNS lymphoma, ependymoma, haemangioblastoma, medulloblastoma, meningioma, glioma, mixed glioma, oligodendroglioma, pineal region tumors and pituitary tumors. Gliomas are tumors of the glial cells; these cells support and protect nerve cells in the brain. Gliomas comprise nearly half of all primary brain tumors and a fifth of all primary spinal cord tumors.

The therapy of the invention is particularly useful where the brain tumor is a glioma tumor, more particularly glioblastoma multiforme (GBM).

The term "tumor" and "cancer" may be used interchangeably herein. Reference to a "glioma" includes GBM, astrocytoma, anaplastic astrocytoma, mixed glioma, oligodendroglioma or related brain cancers including glioblastoma-initiating cells (GICs).

The "pharmaceutical product" is according to claim 1. In some particular embodiments the product comprises the combination of L-2,4-diaminobutyric acid (DAB) and prazosin.

A "(pharmaceutical) product" in the context of the present invention also includes multi-part such as a two-part composition where the active agents L-2,4-diaminobutyric acid (DAB) and prazosin are provided separately and given or dispensed separately or admixed together prior to dispensation. For example, a multi-part pharmaceutical pack may have the two or three active agents separately maintained.

The product may comprise at least one additional therapeutic agent.

The term "additional therapeutic agent", as used herein, is used in its broadest sense and includes any substance or mixture of substances different from L-2,4-diaminobutyric acid (DAB) and prazosin, that provides clinical use, or that, when taken up by the body, or introduced into the body, of a living organism, alters normal bodily or cellular function. An additional therapeutic agent can be any agent that provides a therapeutic or prophylactic effect, a compound that affects or participates in tissue growth, cell growth, cell differentiation, a compound that may be able to invoke a biological action such as an immune response, or could play any other role in one or more biological processes. In some particular embodiments, the therapeutic agent is such as amino acids, peptides, polypeptides, proteins, polysaccharides, muteins, immunoglobulins, antibodies, cytokines (e.g., lymphokines, monokines, chemokines), blood clotting factors, hemopoietic factors, interleukins (1 through 18), interferons (e.g., β-IFN, α-IFN and γ-IFN), erythropoietin, nucleases, tumor necrosis factor, colony stimulating factors (e.g., GCSF, GM-CSF, MCSF), insulin, antitumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone, luteinizing hormone releasing factor), vaccines (e.g., tumoral, bacterial and viral antigens); statins (like lovastatin, simvastatin, atorvastatin etc), somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; cells, viruses, anti-tumoral antibodies, antigens and antigen fragments, tumor cell and tumor cell fragments (fragments of tumor which may invoke an immune response to the tumor), stem cells, exosomes and ribosomes.

Also some non-limiting examples of suitable additional therapeutic agents including combinations and alternative forms of them, include: analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate); antiasthmatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, doxepin, amoxapine, trazodone, amitriptyline, maprotiline, phenelzine, desipramine, nortriptyline, tranylcypromine, fluoxetine, imipramine, imipramine pamoate, isocarboxazid, trimipramine, and protriptyline); antidiabetics (e.g., biguanides and sulfonylurea derivatives); antifungal agents (e.g., griseofulvin, ketoconazole, itraconazole, amphotericin B, nystatin, and candicidin); antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, *Rauwolfia serpentina*, alseroxylon, and phentolamine); anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, deflazacort, celecoxib, rofecoxib, hydrocortisone, prednisolone, and prednisone); antineoplastics (e.g., cyclophosphamide, actinomycin, bleomycin, dactinomycin, daunorubicin, doxorubicin, epirubicin, mitomycin, methotrexate, fluorouracil, gemcitabine, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, goserelin, leuprolide, tamoxifen, interferon alfa, retinoic acid (ATRA), nitrogen mustard alkylating agents, and piposulfan); antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., ergotamine, propanolol, isometheptene mucate, and dichloralphenazone); sedatives/hypnotics (e.g., barbiturates such as pentobarbital, pentobarbital, and secobarbital; and benzodiazepines such as flurazepam hydrochloride, triazolam, and midazolam); antianginal agents (e.g., beta-adrenergic blockers; calcium channel blockers such as nifedipine, and diltiazem; and nitrates such as nitroglycerin, isosorbide dinitrate, pentearythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine); antimanic agents (e.g., lithium carbonate); antiarrhythmics (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine); antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibrinolytic agents (e.g., aminocaproic acid); hemorheologic agents (e.g., pentoxifylline); antiplatelet agents (e.g., aspirin); anticonvulsants (e.g., valproic acid, divalproex sodium, phenytoin, phenytoin sodium, clonazepam, primidone, phenobarbital, carbamazepine, amobarbital sodium, methsuximide, metharbital, mephobarbital, mephenytoin, phensuximide, paramethadione, ethotoin, phenacemide, secobarbital sodium, clorazepate dipotassium, and trimethadione); antiparkinson agents (e.g., ethosuximide); antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and); agents useful for calcium regulation (e.g., calcitonin, and parathyroid hormone); antibacterial agents (e.g., amikacin sulfate, aztreonam, chloramphenicol, chloramphenicol palmitate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime axetil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; macrolides such as, azithromycin, clarithromycin, and erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride); anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and theophylline; mast cell stabilizers such as cromolyn sodium; inhalant corticosteroids such as beclomethasone (BDP), and beclomethasone dipropionate monohydrate; salbutamol; ipratropium bromide; budesonide; salmeterol; xinafoate; triamcinolone; nedocromil sodium; flunisolide; fluticasone propionate; steroidal compounds and hormones (e.g., androgens such as danazol, testosterone cypionate, fluoxymesterone, ethyltestosterone, testosterone enathate, methyltestosterone; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and thyroid hormones such as levothyroxine sodium); hypoglycemic agents (e.g., human insulin, purified beef insulin, purified pork insulin, glyburide, metformin, chlorpropamide, glipizide, tolbutamide, and tolazamide); hypolipidemic agents (e.g., clofibrate, dextrothyroxine sodium, probucol, pravastatin, atorvastatin, lovastatin, and niacin); proteins (e.g., DNase, alginase, superoxide dismutase, and lipase); nucleic acids (e.g., sense or anti-sense nucleic acids encoding any therapeutically useful protein, including any of the proteins described herein); agents useful for erythropoiesis stimulation (e.g., erythropoietin); antiulcer/antireflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); as well as other drugs useful in the compositions and methods described herein include mitotane, halonitrosoureas, anthrocyclines, ellipticine, ceftriaxone, ketoconazole, ceftazidime, oxaprozin, valacyclovir, urofollitropin, famciclovir, flutamide, enalapril, itraconazole, buspirone, gabapentin, fosinopril, tramadol, acarbose, lorazepam, follitropin, omeprazole, fluoxetine, lisinopril, tramadol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainide, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide, including combinations and alternative forms thereof, such as alternative salt forms, free acid form, free base forms, pro-drugs and hydrates.

In some embodiments, the additional therapeutic agent may be water soluble. In some embodiments, the additional therapeutic agent may not be water soluble.

In some embodiments, the therapeutic agent may be selected from corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, and prednisolone sodium phosphate.

Various forms of the other therapeutic agents may be used. These include, without limitation, such forms as uncharged molecules, molecular complexes, salts, ethers, esters, amides, and the like, which are biologically activated when injected or inserted into the tumor.

The terms "effective amount", "effective concentration" and "therapeutically effective amount" of the at least two active agents as used herein mean a sufficient amount of the at least two agents to provide the desired therapeutic or physiological effect or outcome. Such an effect or outcome includes inhibiting the growth or viability of cells associated with a cancer. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount" or "effective concentration". However, an appropriate "effective amount" or "effective concentration" in any individual case may be determined by one of ordinary skill in the art using only routine experimentation.

The effective amount is deemed the amount of the at least two active agents required to inhibit the growth or viability of cells associated with a cancer. The effective concentration (for example when the product is administered intratumorally) is deemed the concentration of the at least two active agents in the product, required to inhibit the growth or viability of cells associated with a cancer.

According to particular embodiments, for intratumoral delivery, the effective concentration of the combination of L-2,4-diaminobutyric acid (DAB) and prazosin includes, respectively, from about 50 mM to about 300 mM of L-2,4-diaminobutyric acid (DAB) and from about 1 μM to about 500 μM (500 μM) of prazosin.

The combination for use according to the invention is administered by the novel drug delivery method which comprises the infusion of the combination through one or more catheters left inside the tumor, the tumor's resection cavity, or biopsy site, at a total flow rate of ~3 ml/hour, with periodical interruptions for repeated sessions of drainage and infusion of 1-2 ml of a physiological isotonic fluid and, or, with isotonic Tris buffer, pH 7.2-9.1. Typically, the number of interruptions for drainage and infusion is based on the patient's individual parameters.

The administration is either continuous or is periodically interrupted. The administration of the active agents may be simultaneously or separately in any order. Doses may be administered intratumorally over a certain period of time, e.g. some days, through one or more catheters at different flow rates. Periodical tumor bed irrigation with an alkaline Tris buffer, pH 7.2-9.1, for cellular debris' and inactive metabolites' evacuation, through one of the indwelling catheters, is desirable, as to maximize the active drug-target cell's interface.

The flow rate of administration can vary within a broad range. Lower flow rates are used for continuous administration whilst interrupted administration usually requires higher to much higher flow rates. Typically flow rates from 1 μl/min to 3 ml/s, in particular from 1 μl/min to 2 ml/s, or from 5 μl/min to 1 ml/s, or from 10 μl/min to 0.5 ml/s may be used.

"Treating" a subject involves altering the natural course or biological behavior of a cancer in an affected subject as well as treatment of a clinically asymptomatic subject having biochemical or immunological markers of a possible or developing tumor, to the benefit of the subject. In one particular embodiment, the present invention contemplates a reduction of the growth or viability of cells associated with a cancer.

The "subject" as used herein refers to an animal, preferably a mammal and more preferably a primate including a lower primate and even more preferably a human who can benefit from the products and methods of the present invention. A subject regardless of whether a human or non-human animal may be referred to as an individual, patient, animal, host or recipient. The agents and methods of the present invention have applications in human medicine, veterinary medicine as well as in general, domestic or wild animal husbandry. For convenience, an "animal" includes an avian species such as a poultry bird (including ducks, chicken, turkeys and geese), an aviary bird or game bird.

The condition in a non-human animal may not be a naturally occurring but induced such as in an animal model.

As indicated above, the preferred animals are humans, non-human primates such as marmosets, baboons, orangutan's, lower primates such as tupaia, livestock animals, laboratory test animals, companion animals or captive wild animals. A human is the most preferred target. However, non-human animal models may be used.

Examples of laboratory test animals include mice, rats, rabbits, guinea pigs and hamsters. Rabbits and rodent animals, such as rats and mice, provide a convenient test system or animal model as do primates and lower primates. Livestock animals include sheep, cows, pigs, goats, horses and donkeys. Non-mammalian animals such as avian species, zebrafish, amphibians (including cane toads) and *Drosophila* species such as *Drosophila melanogaster* are also contemplated. Instead of a live animal model, a test system may also comprise a tissue culture system.

In some particular embodiments subjects are preferably a human with suspected brain tumor, therapy-naive or previously undergone treatment who received a standard biopsy or surgical open craniotomy and decompression under local or general anaesthesia, to be followed or not by radiotherapy and/or chemotherapy. More preferably, subjects with suspected glioblastoma, therapy-naive or previously undergone treatment who received a standard biopsy or surgical open craniotomy and decompression under local or general anaesthesia.

In some embodiments, subjects are preferably a human eligible for tumor removal or have had their brain tumor completely excised.

In some other embodiments, subjects eligible for the treatment of the present invention present the tumor deep in the brain or the tumor infiltrates brain tissue, so that the tumor may be debulked rather than removed.

Pharmaceutical Formulations

The formulations herein described, comprising L-2,4-diaminobutyric acid (DAB) and prazosin, are for use in the treatment of a cancer.

Said formulations may further comprise one or more pharmaceutically acceptable carriers in which the active agents are mixed, dissolved, suspended, emulsified or the like.

According to particular embodiments, the formulations of the present invention comprise one or more additional therapeutic agents.

A "pharmaceutically acceptable carrier" includes any and all solvents, dispersion media, coatings, isotonic and absorption delaying agents, buffering agents, and the like, preferably compatible with intratumoral administration. Particularly useful examples of such carriers include, but are not limited to, water, saline, buffers (Tris, and Hanks, Sorensen's) surfactants (tweens, pluronics, etc.), dispersing agents, Ringer's Lactate solutions and dextrose solution. For intratumoral injection, Tris buffered aqueous solution or phosphate buffered saline may be suitable carriers for the compositions described herein. It is envisioned that the volume of the pharmaceutical carrier may vary according to the specific active agents selected and their respective solubilities with the carrier.

The formulations described herein are formulated to be compatible with the route of intratumoral administration. Solutions, suspensions, dispersions, emulsions, mixtures and the like, may be used for such administrations and may include a sterile diluent, such as water for injection, saline solution, polyethylene glycols, glycerine, propylene glycol or other synthetic solvents; anti-bacterial agents such as benzyl alcohol or methylparabens; antioxidants such as ascorbic acid or sodium bisulfite; buffers such as Tris (tris(hydroxymethyl)aminomethane), acetates, citrates or phosphates, and agents for the adjustment of tonicity such as sodium chloride or dextrose. The pH of the formulation may vary between 7.2 and 8.1, preferably between 7.5 and 7.7, and more preferably is 7.55-7.60. The pH value may be adjusted with acids or bases, such as hydrochloric acid or sodium hydroxide.

The additional therapeutic agent can be, in some examples, incorporated to the formulations of the invention for intratumoral administration together with L-2,4-diaminobutyric acid (DAB) and prazosin. The therapeutic agent may be incorporated into the formulation in any physical form suitable for intratumoral delivery. Some non-limiting examples include powders, particles, fibers, beads, microspheres, solutions, suspensions, and the like. In other embodiments the additional therapeutic agent is not incorporated into the formulation of the invention, and is administered also intratumorally in a separate manner, e.g., from another preparation.

The formulation of the invention may be prepared by methods well known in the art of pharmacy and conveniently be presented in a unit dosage form for intratumoral administration e.g. enclosed in ampules, disposable syringes or multiple dose vials made of glass or plastic.

Accordingly, some methods for preparation include a step of separately bringing into association each of the active agents L-2,4-diaminobutyric acid (DAB) and prazosin with a carrier or carriers.

In some other methods, the two active ingredients, L-2,4-diaminobutyric acid (DAB) and prazosin are brought together in association with a carrier or carriers.

Typically the formulations are prepared by processes well known to the skilled person in the art. Processes may comprise mixing, dissolving, emulsifying, suspending or the like, the active agents in a liquid carrier, optionally comprising other excipients, like pH buffering agents, preservatives, and the like, followed by sterilization. Any suitable method of sterilization may be used including steam sterilization, sterile filtration, chemical sterilization, such as exposure to ethylene oxide, and radiation sterilization, such as gamma radiation, electron beam processing, and ultraviolet light irradiation. The formulations are then packaged in a unit dosage form for intratumoral administration e.g. enclosed in ampules, disposable syringes or multiple dose vials made of glass or plastic.

L-2,4-diaminobutyric acid (DAB) is soluble in aqueous media. However, prazosin is not, for which reason for the preparation of the formulations of the invention these active agents may be first dissolved in an adequate amount of an organic solvent, and the resulting solutions then diluted with aqueous carrier or with DAB solution. Examples of organic solvents used for dissolving prazosin are DMSO, dimethylformamide, ethanol, methanol, and the like. Organic solvents may be thus present in the preparations in reduced amounts typically comprising between 0.01% and 2%, optionally between 0.01% and 1% by weight in respect of the total weight of the preparation.

According to some embodiments the method for the preparation of the formulations of the invention comprises:

a) dissolving L-2,4-diaminobutyric acid (DAB) in aqueous carrier;

b) dissolving prazosin in an organic solvent and diluting the resulting solution with aqueous carrier In some embodiments the method comprises steps a) and b) and formulations comprising L-2,4-diaminobutyric acid (DAB) and prazosin are obtained. Optionally the aqueous carrier used in b) is the resulting product of step a), e.g. the aqueous solution comprising L-2,4-diaminobutyric acid (DAB).

The formulations may comprise different concentrations of each of the active agents.

There is no critical upper limit on the amount of the active agents incorporated in the formulation except for that of an acceptable solution or dispersion to maintain the physical characteristics desired for the composition. The lower limit of the active agents incorporated into the delivery system is dependent upon the activity of the drug and the length of time needed for treatment. Thus, the amount of the active agents should not be so small that it fails to produce the desired therapeutic effect, nor so large that the active agents are released in an uncontrollable manner.

The concentration of each of the active agents may vary between broad ranges; there is no particular limitation in respect of their concentrations. However, typically the concentrations are between 50 mM and 300 mM of L-2,4-diaminobutyric acid (DAB), to maintain the concentration advantage over the physiological amino acids in the microenvironment of the tumor, and between 1 μM and 500 μM of prazosin.

In some embodiments the concentrations are between 75 mM and 145 mM of L-2,4-diaminobutyric acid (DAB) and between 10 μM and 100 μM of prazosin.

In some other embodiments the concentrations are between 80 and 140 mM of L-2,4-diaminobutyric acid (DAB), preferably 130 mM and between 20 and 80 μM of prazosin, preferably 50 μM As previously mentioned in the context of the present invention the product of the invention also includes multi-part such as a two-part composition where the active agents L-2,4-diaminobutyric acid (DAB) and prazosin are provided separately and given or dispensed separately or admixed together prior to dispensation. For example, a multi-part pharmaceutical pack may have the two or three active agents separately maintained.

In addition, L-2,4-diaminobutyric acid (DAB) and prazosin may be administered to the subject by different routes.

The products and compositions of the invention can be included in a kit, container, pack or dispenser, together with medical devices suitable for delivering the compositions intratumorally. The compositions included in kits may be supplied in containers of any sort such that the life of the different components may be preserved and may not be adsorbed or altered by the materials of the container. For example, sealed glass ampules or vials may contain the compositions described herein that have been packaged under a neutral non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include bottles that are fabricated from similar substances as ampules, and envelopes that consist of foil-lined interiors, such as aluminum or an alloy. Other containers include test tubes, vials, flasks, bottles, syringes, etc. Some containers may have a sterile resealable access port, such as a bottle having a stopper that may be pierced repeatedly by a hypodermic injection needle.

The pharmaceutical products according to the invention may be administered intratumorally in a therapeutically effective dose. Amounts effective for this use will, of course, depend on the severity of the disease and the weight and general state of the subject. For treatment of a subject, depending on activity of the active agents, nature and severity of the disorder, age and body weight of the subject, different daily doses of the combination of the at least two active ingredients selected from L-2,4-diaminobutyric acid (DAB) and prazosin can be administered. Under certain circumstances, however, higher or lower daily doses may be appropriate.

The product may be administered by a variety of methods. For example, it may be injected directly into the solid tumor being treated with a needle, such as a Turner Biopsy Needle or a Chiba Biopsy Needle; or maybe injected directly by means of a catheter at different flow rates after open craniotomy and decompression or through a burr hole cranioanatresis, depending on the circumstances of the subject to be treated.

In some embodiments the product is intratumorally administered through a catheter previously inserted in a subject. The flow rate of administration is established taking into account the circumstances of the subject such as the subject's intracranial or intra abdominal or intrathoracic pressure and other factors, like the positioning of the catheter's tip and the general or neurological status of the subject.

Typically, the flow rate of the administration of the product can vary within a broad range, typically from 1 μl/min to 3 ml/s, in particular from 50 μl/min to 2 ml/s, or from 100 μl/min to 1 ml/s, or from 250 μl/min to 0.5 ml/s.

There is still further provided a method for the treatment of a cancer which comprises the intratumoral administration of a product comprising L-2,4-diaminobutyric acid (DAB) and prazosin to a subject in need thereof.

According to some embodiments the method of treatment comprises the intratumoral administration of L-2,4-diaminobutyric acid (DAB) and prazosin.

The administration of different combinations of active agents in the method of treatment of the invention can be in any order.

The method of treatment of the invention can be carried out on a subject in need thereof for a period of time e.g. a number of days which may vary depending on activity of the active agents, the nature and severity of the disorder, age and body weight of the subject, or different daily doses of L-2,4-diaminobutyric acid (DAB) and prazosin. Typically, treatment is carried out for a period of between 2 and 20 days, for example for periods between 4 and 16 days, or 7 and 14 days.

The same or different combinations of the two active agents can be given during any treatment period.

The "subject" as previously mentioned is preferably a mammal and more preferably a human who can benefit from the products and methods of the present invention, also referred to as patient.

In some particular embodiments the patient is a human with suspected glioblastoma, therapy-naive or previously undergone a cancer treatment who receives a standard biopsy after cranioanatresis under local or general anaesthesia.

After biopsy samples are taken, catheter(s) are implanted following the same path of the biopsy stylet, as to minimize trauma. Alternatively the catheters are implanted as to be biased and create a pressure gradient when in use for infusion and drainage. After a confirmation of the diagnosis by frozen section, administration of the drug combination—at flow rates based on the patient's intracranial pressure, clinical course and neuro-radiologic imaging of tumor necrosis and brain oedema-takes place.

In some other embodiments the patient is a human eligible for tumor removal who receives a standard operation under general anaesthesia and catheter(s) are left into the tumor's resection bed. After a confirmation of the diagnosis by frozen section, administration of the therapeutic solution takes place, at flow rates based on the patient's intracranial pressure, clinical course and neuro-radiologic imaging of any residual tumor necrosis and brain oedema.

In some particular embodiments the patient is a human with suspected body cancer, therapy-naive or who has previously undergone a cancer treatment, who receives a standard, ultrasound or CT guided, transcutaneous biopsy under local or general anaesthesia.

After biopsy samples are taken, catheter(s) are implanted following the same path of the biopsy stylet to minimize trauma. Alternatively the catheters are implanted as to be biased and create a pressure gradient when in use for infusion and drainage. After a confirmation of the diagnosis by frozen section, start of the product's administration at flow rates based on the patient's individual parameters.

In some other embodiments the patient is a human eligible for body tumor removal who receives a standard operation under general anaesthesia and catheter(s) are left into the tumor's resection bed. After a confirmation of the diagnosis by frozen section, administration of the therapeutic solution takes place, at flow rates based on the patient's individual parameters.

By employing the products and delivery methods described herein, the at least two active agents may be initially localized within the confines of the tumor thereby enhancing the local effect of the active agents contained inside the tumor while the blood-levels of the active agents outside the perimeter of the tumor remain low. In this way, an enhanced therapeutic gain may be achieved. The therapeutic effect on the tumoral cells is greater; additionally, susceptible normal cells remote from the administration site may be more or less affected. Accordingly, the active agents are employed in a manner which is less systemic, i.e., directed more specifically towards the cancerous cells, while simultaneously protecting sensitive normal cells, both in the vicinity of and distant from the site of the cancerous cells.

The method of treatment of the invention can also comprise the administration of one or more additional therapeutic agents.

The additional therapeutic agent can be, in some examples, incorporated to the formulations of the invention for intratumoral administration. The therapeutic agent may be incorporated into the product in any physical form suitable for intratumoral delivery. Some non-limiting examples include powders, particles, fibers, beads, microspheres, solutions, suspensions, and the like. In other embodiments the additional therapeutic agent is not incorporated into a formulation of the invention, and is administered also intratumorally, either simultaneously or sequentially, from another preparation.

In other examples the additional therapeutic agent can be administered simultaneously or sequentially by any other different route of administration, e.g. oral, topical, parenteral, intravenous, inhalation, and the like.

Examples of therapeutic agents which may be utilized in accordance with the present disclosure are as described above.

In general the additional therapeutic agent can also be administered during the whole period of treatment, or at intervals or at points of time during treatment.

The additional therapeutic agent may be used in amounts that are therapeutically effective, which varies widely depending largely on the particular additional therapeutic agent being used.

In some embodiments the additional therapeutic agent can be intratumorally administered through the same or a different lumen of the catheter(s). This depends for example on the number of catheters, the positioning of the catheter's tip, the subject's intracranial pressure and other factors. The flow rate of administration can vary within a broad range, typically from 1 μl/min to 3 ml/s, in particular from 5 μl/min to 2 ml/s, or from 100 μl/min to 1 ml/s, or from 250 μl/min to 0.5 ml/s.

Without willing to be bound to any theory, the present inventors believe that a main reason of the lack of clinical efficiency of previous attempts to deliver local chemotherapy to gliomas, is the protection of the malignant cells by a volume of inactive drug metabolites and cellular debris produced from previous drug action: the central nervous system's extracellular space has no transport proteins and the raised intracranial pressure and chaotic cytoarchitecture of glioblastomas contribute in maintaining this inactive fluid between the infusion catheter's tip and the next malignant cell layer.

Thus according to some embodiments the method of treatment of the invention may comprise one or more steps of drainage and irrigation periods of the fluid around the catheter(s)' tip(s)—produced from cellular debris and inactive products of previous drug-tissue interaction—in order to achieve maximum contact of the active agents and the target cells (also enhanced by the diffusion and convection forces created during the periodical drainage-infusions of drugs and physiologic fluids), as well as for reducing local pressure and acidity. This way the concentration of the active agents in contact with the malignant cell's membrane will remain high and the active agent-cell interaction will take place under improved physicochemical circumstances, especially when isotonic Tris buffer, pH7.2-9.1 is used in order to reverse the acidity of the tumor's extracellular space.

These steps of drainage and irrigation periods are particularly advisable in subjects where surgical excision of the tumor is not possible or suboptimal.

The present invention is based at least in part on the following studies.

1. Preparation of a Formulation: 130 mM L-2,4-Diaminobutyric Acid (DAB) and 50 μM Prazosin L-2,4-diaminobutyric acid and Prazosin are available on the market from several approved vendors.

L-2,4-diaminobutyric acid (DAB, dihydrochloride form, MW 191.06) was dissolved in water to a final concentration of 130 mM. Prazosin was first dissolved in DMSO at a concentration of 25 mM, and to the resulting solution the 130 mM L-2,4-diaminobutyric acid (DAB) solution was added under stirring to achieve a final concentration of Prazosin of 50 μM. Then the pH of the Prazosin and DAB solution was adjusted to pH of 7.55 (37° C.) with pH buffering agent Tris-base.

An isotonic Tris-buffered solution at pH 8.1 was also prepared in order to periodically (every 2 hours) infuse a few ml intratumorally, as to enhance the above solution's action.

This periodical infusion is done after allowing 1-2 minutes for gravity drainage or manual aspiration of a few ml, to maintain the intracranial pressure at the same level despite the infusion. This procedure with 1-2 ml aspiration and 1-2 ml infusion is preferably repeated gently several times for about 5 minutes every 2 hours with or without interruption of the drug's infusion (in case we have more than one catheter intratumorally).

2. Study: In Vitro Efficacy of the Drug Combinations on Glioma and Normal Cell Lines The ability of combinations of two drugs, L-2,4 Diaminobutyric Acid (DAB) and Prazosin, to inhibit the growth, in vitro, of two cell lines: i) LN-18, a human line derived from a grade IV glioblastoma patient and ii) HMC3, a human brain non-malignant cell line, which retains the properties of primary microglial cells has been investigated.

Two colorimetric assays were established to monitor cytotoxicity in response to the tested drugs, one measuring the release of lactate dehydrogenase (LDH) from cells, a well-established marker for cell toxicity, and the other measuring the activity of mitochondrial lactate dehydrogenase, an indicator of cell viability, by the reduction of the soluble tetrazolium dye MTT. Both assays gave similar results in terms of their ability to measure cytotoxicity and consequently, the LDH assay was chosen for further experiments. Cells were also monitored by direct microscopic observation. Controls included cells treated with medium without drug and cells treated with Camptothesin, a known cytotoxic agent, as positive control. Incubation with drug concentrations was carried out for 24 hours at 37° C.

Figure 2:
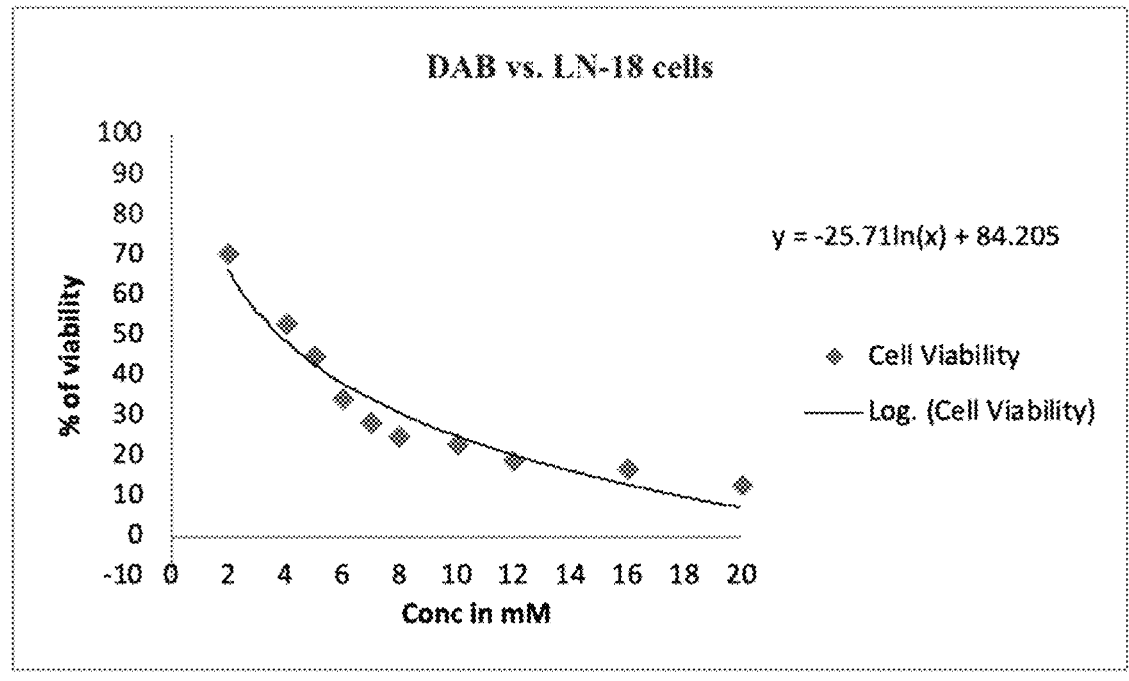
FIG. 2 shows a dose-response effect of DAB on viability of cultured LN-18 cells.

DAB was tested in vitro under ideal conditions in absence of any competing physiological amino acid allowing low concentrations of 0.5, 1, 2, 3, 4, 5, 6, 8, 12, and 16 mM. As shown in FIGS. 1 and 2, DAB demonstrated weak toxicity towards the non-malignant HMC3 cells (no IC50 could be determined) and a strong cytotoxic effect against the glioma cell line LN-18 (IC50=3.8 mM).

Figure 3:
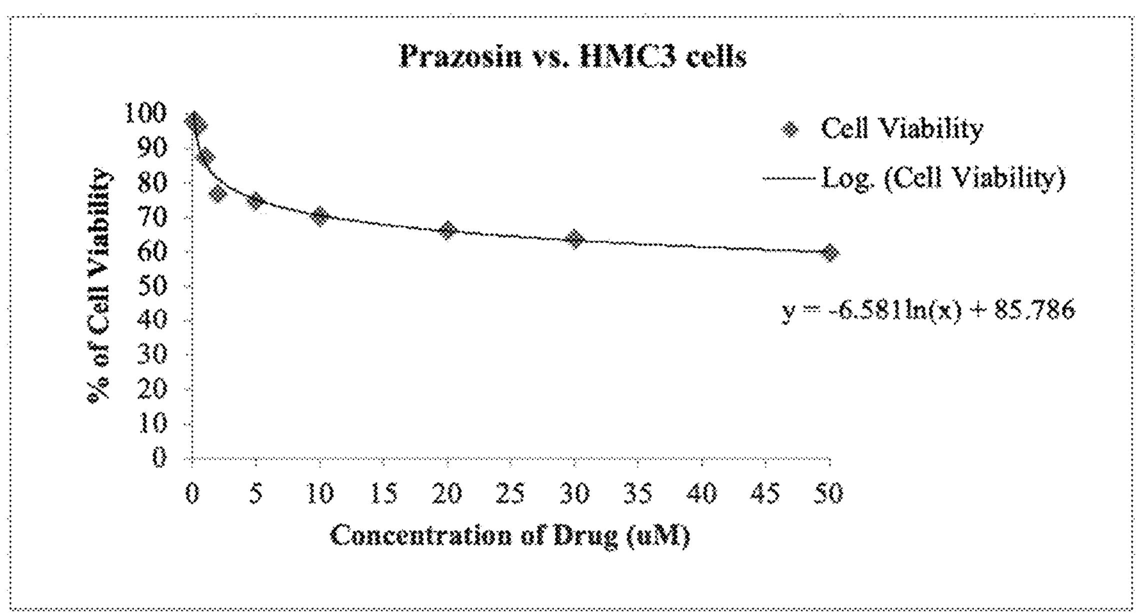
FIG. 3 shows a dose-response effect of Prazosin on viability of cultured HMC3 cells.
Figure 4:
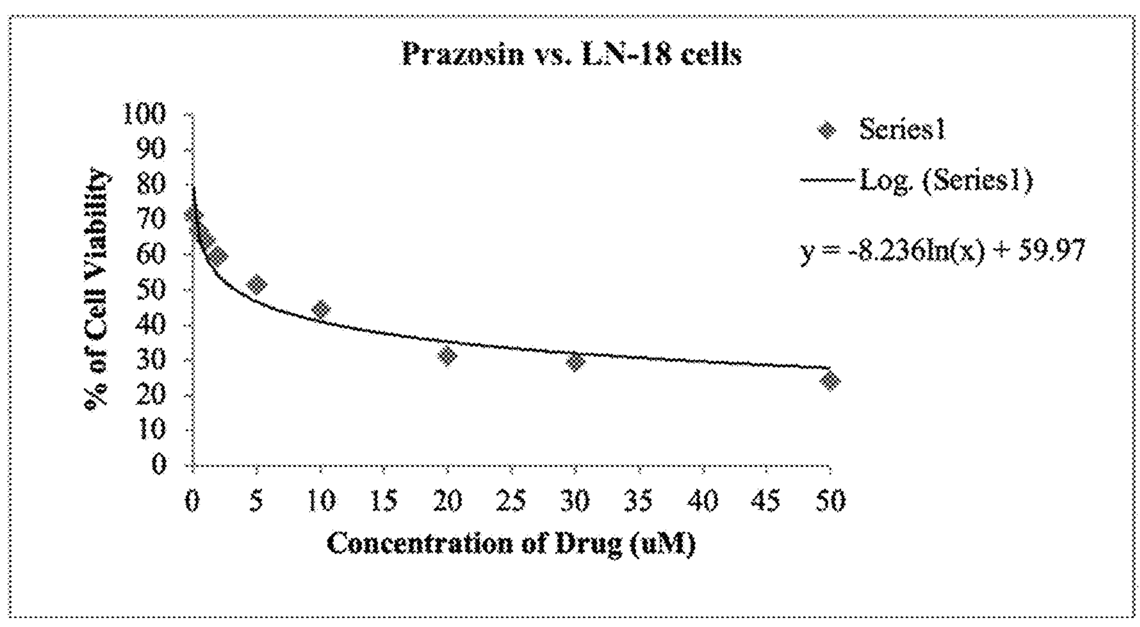
FIG. 4 shows a dose-response effect of Prazosin on viability of cultured LN-18 cells.

Prazosin was tested at concentrations of 0.1, 0.5, 1, 2, 5, 10, 20, 30 and 50 μM. Similarly, to DAB, this compound showed little cytotoxicity against the non-malignant HMC3 line (FIG. 3, no IC50 could be determined) and a strong cytotoxic effect against the glioma LN-18 line (FIG. 4; IC50=3.4M).

Figure 5:
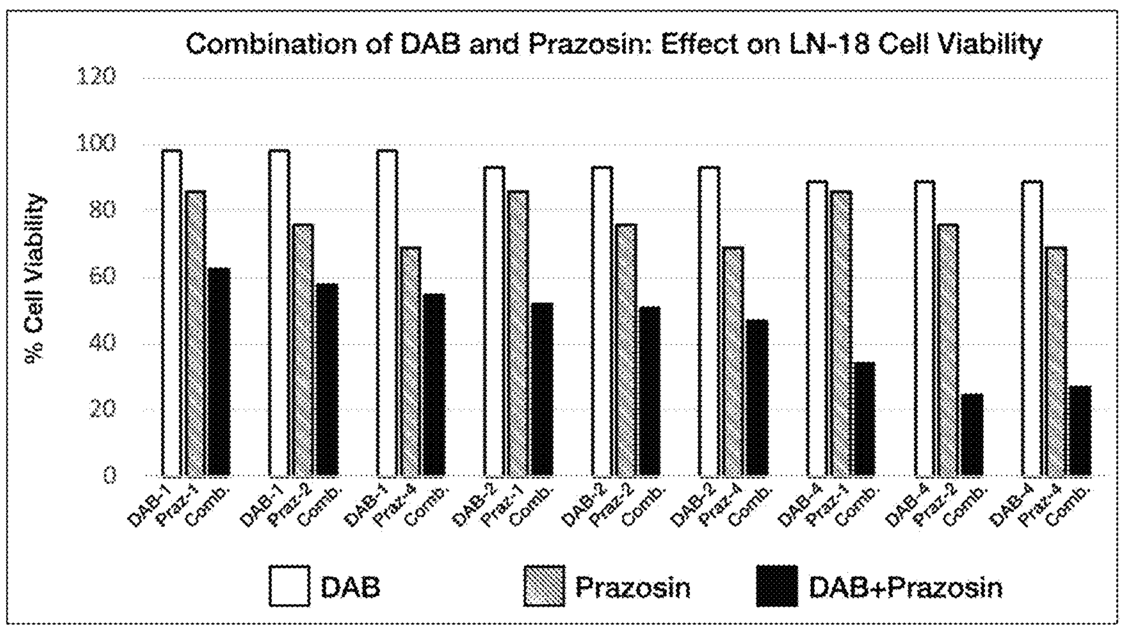
FIG. 5 shows the effect of DAB, Prazosin and combinations of DAB and Prazosin on LN-18 Cell Viability.
Figure 6:
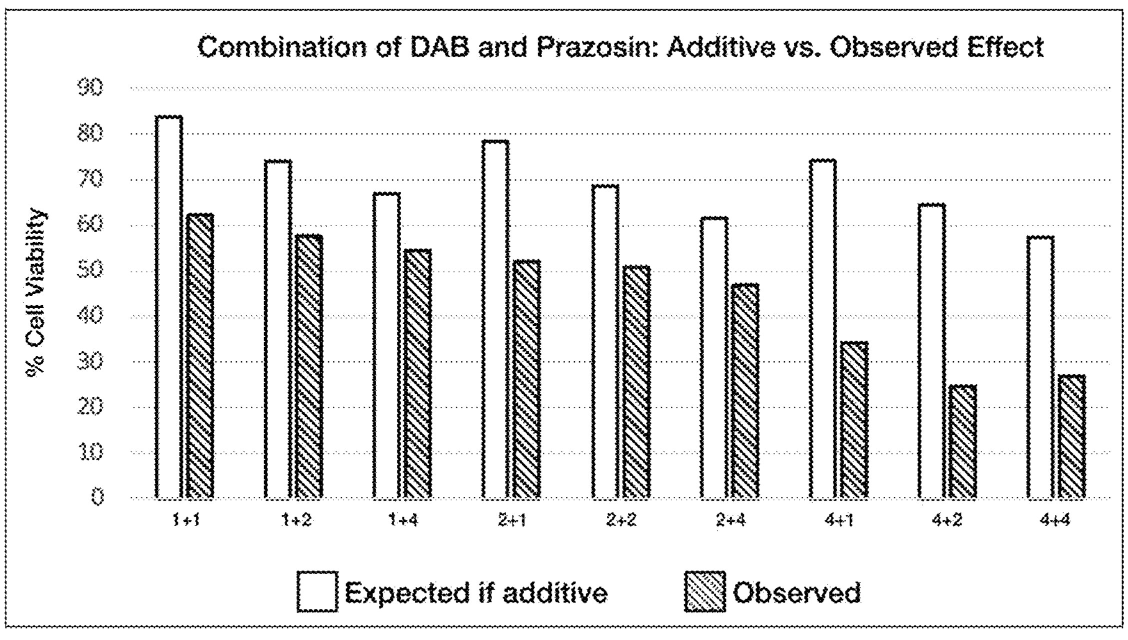
FIG. 6 shows the comparison between the observed effect and the expected effect (if additive) on cell viability for combinations of DAB and Prazosin.

Based on the above results with single drugs, we investigated the efficacy of drug combinations to unravel possible synergistic effects. DAB was used at concentrations of 1, 2 and 4 mM. Each of these concentrations was tested alone or in combination with 1, 2 or 4 μM of Prazosin, i.e. the combinations tested were the following:

1 mM DAB+1 μM Prazosin
1 mM DAB+2 μM Prazosin
1 mM DAB+4 μM Prazosin
2 mM DAB+1 μM Prazosin
2 mM DAB+2 μM Prazosin
2 mM DAB+4 μM Prazosin
4 mM DAB+1 μM Prazosin
4 mM DAB+2 μM Prazosin
4 mM DAB+4 μM Prazosin FIG. 5 compares the effect of either drug alone (white for DAB, grey for Prazosin) to the effect of the drug combination (black). The results show that the combined use of the two drugs has a more potent effect than the additive effect of the two drugs alone. For clarity, this is further pictured in FIG. 6, which compares the expected cell viability for an additive effect, i.e. simply adding the effect of the two drugs alone (white) to the observed effect (grey), showing that the latter is clearly stronger, indicating a synergistic effect.

Figure 7:
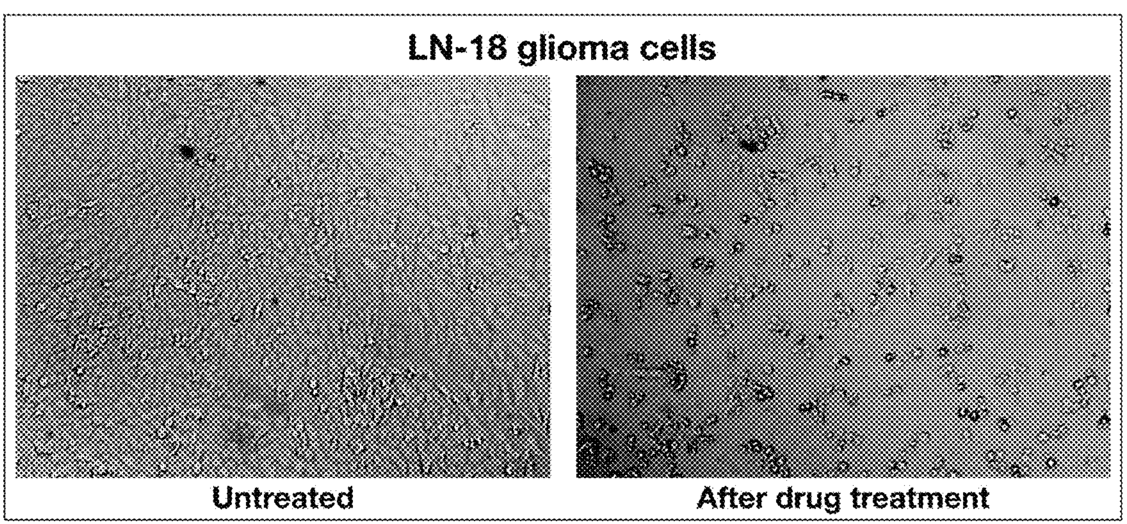
FIG. 7 shows a phase-contrast micrograph of LN-18 cells before and after treatment with DAB/Prazosin combination.

The results were further confirmed with direct microscopy, as shown in FIG. 7.

The data presented shows that combinations of DAB and prazosin exert a cytotoxic action against a human glioma cell line but not against a non malignant glioma cell line and that there is a synergistic effect.

3. Clinical Study: Intratumoral Administration of DAB to 5 Glioma Patients

The clinical course of 5 glioma grade IV patients was studied. All the patients underwent craniotomy and gross total removal of their tumor and were treated with postoperative intratumoral administration of DAB, through a usual drainage or extra ventricular catheter (EVD) left in the cavity of the resected tumor, for 2-5 days. The catheter was connected to an intravenous drug delivery pump (SMITHS) and the flow rate was 1-3 ml/hour (depending on patient's status and lesion's volume). Every two hours the neurosurgeon on duty interrupted the treatment in order to aspirate, by gravity and, or, manually, necrotic fluid from the infusion site and infuse manually physiological fluid (Ringer's solution).

The patients are followed up, both clinically as well as with MRI imaging.

4. Clinical Study: Intratumoral Administration of DAB and Prazosin to One Glioma Patient Using the Novel Drug Delivery Method.

This 36-year-old lady operated for right fronto parietal high grade lesion (glioblastoma multiforme) presented with a large recurrence in the operated areas within 3 months. She had symptoms of raised intracranial pressure with left hemiparesis. After preoperative assessment and imaging, she underwent surgery on Aug. 11, 2017. Re-exploration of the craniotomy and gross total removal of the tumor was done. Since it was a recurrence within a short time, with a 26 Oct. 2017 immunohistochemistry report as a Glioblastoma, IDH1 (R132H) mutant, WHO Grade glioma IV, and intra operatively looked like a very aggressive and high grade tumor, a catheter was placed in the cavity. After proper explanation and consent from spouse, an intratumoral infusion of an isotonic drug solution (containing 130 mM L-2,4-diaminobutyric acid (DAB) and 50 μM Prazosin, with pH of 7.55 at 37° C.), was administered for 96 hours (13-16 Nov. 2017), at 3 ml/h, inside the postoperative cavity. Every 2 hours there was a five minute interruption, as to alternatively infuse and aspirate manually many times through a 5 ml syringe: infuse a 1-2 ml volume of an isotonic Tris-buffered solution at pH 8.1 and aspirate 1-2 ml of the necrotic fluid produced from the drug-malignant cell interaction. The patient was continuously monitored for any side effects during treatment.

She tolerated the treatment very well and was discharged on a stable state on 20 Nov. 2017.

She has been followed up serially, both clinically as well as with MRI imaging.

Follow Up Report with Visit Dates:

8 Dec. 2017—She has clinically improved. There were no symptoms. Left hemiparesis has improved. She had occasionally left focal seizures involving the upper limb. She was on Temozolomide chemotherapy.

1 Jan. 2018—She completely recovered. There was Left hemiparesis with ability to ambulate without support. Marked reduction in left upper limb focal seizures. Adjuvant Temozolomide chemotherapy continued.

6 Feb. 2018—She recovered completely with no neurological deficits. She is able to carry out activities of daily living independently. Adjuvant Temozolomide chemotherapy continued.

7 Mar. 2018—She remained in the same stable state. Adjuvant Temozolomide chemotherapy continued.

7 May 2018—She complained of mild unsteadiness. No neurological deficits. Occasional focal seizures involving the left upper limb. MRI no evidence of tumor.

14 Jun. 2018—Occasional focal seizure continues. No fresh neurological deficits. Adjuvant TMZ chemotherapy continued.

17 Jul. 2018—Same status, except 2 episode focal seizures.

24 Aug. 2018—Same neurological state.

25 Oct. 2018—No neurological deficits.

15 Jan. 2019—No focal or motor deficits. Independent. Repeat MRI no evidence of tumor 17 Jul. 2020—MRI Report and images dated 14 Jul. 2020. Asymptomatic no focal neurological deficit. Independent and MRI with contrast shows no evidence of tumor.

5. Pilot Study for Intratumoral Administration of DAB and Prazosin to Ten Glioma Patients A clinical study is undergoing ethical and scientific approval (delayed due to Covid-19)—the protocol is described below:

Patients and Method

Number of patients: Ten (10) patients with glioma grade III to IV, therapy-naive or previously undergone treatment.

Age: 20-70 years old both sexes.

No other exclusion criteria apart from general health condition refractory for open craniotomy and/or burr hole cranioanatresis.

After full informed consent, the patient will undergo either a standard craniotomy for tumor resection, or, in case the tumor is considered inoperable, a standard biopsy after cranioanatresis, both to be performed under general anaesthesia.

Post tumor resection or biopsy, one microdialysis catheter, one EVD catheter and one IRRAflow catheter will be left in the resection cavity or will be implanted following the same path of the biopsy stylet, as to minimize trauma.

After a confirmation of the diagnosis by frozen section, the EVD catheter will be connected to an intravenous drug pump and the drug solution will be administered at 3 ml/h. The IRRAflow catheter will be used in order to monitor the intracranial pressure, to infuse periodically an isotonic Tris-buffered solution at pH 8.1 and evacuate the necrotic fluid produced from the drug-malignant cell interaction.

The rate of fluid exchange and the duration of treatment will be individualized based on the patient's intracranial pressure, clinical course, and neuro-radiologic imaging (first MRI at 48 hours from onset of treatment—total predicted treatment time is 5 days—maximum 7 days for big inoperable tumors).

The patient will be monitored for side effects during treatment, including epileptic seizures, drowsiness, worsening of neurological deficits and any other clinical sign.

Before, during and after treatment the patient will be examined neurologically and will have her/his performance status and life quality assessed, according to Karnofsky scale, at bimonthly intervals for at least 12 months. Records of the above clinical follow up will be supplemented with simultaneous MRI examinations performed according to the latest RANO guidelines (https://radiopaedia.org/articles/rano-criteria-for-glioblastoma). These guidelines will apply in order to define for each patient's tumor: location, size, resection extent, cavity size, residual volume, oedema compared to preoperative MRI; and neuroradiological progression In case the patient shows any sign of recurrence in the MRI according to RANO guidelines, adjuvant standard radiotherapy will be performed.

The aims of the study are:

a) to extend the time to recurrence of the tumor, b) to reduce morbidity, c) to better quality of patient's life, d) to extent overall survival time.

L-2,4-diamino-n-butyric acid (dihydrochloride) (DAB) as well as Prazosin are available in the market by different approved vendors. Hospital's pharmacy will prepare the solution containing 100 mmol/L of DAB and 100 μmol/L of Prazosin at pH 7.8, adjusted by addition of Tris-base (Sigma) and Sodium Hydroxide to achieve a concentration of sodium ions (Na+) of 50 mmol/L and an osmolality between 310 and 390 mOsmol/L. There will be no change from the published articles as to the origin of the drugs.

The invention claimed is:

1. A method of treating a brain tumor in a subject comprising administering a combination of L-2,4-diaminobutyric acid (DAB) and prazosin in a therapeutically effective amount to the subject.

2. The method of claim 1, wherein the administering is intratumoral administration to the brain tumor in the subject.

3. The method of claim 1, wherein the brain tumor is selected from acoustic neuroma, astrocytoma, CNS lymphoma, ependymoma, haemangioblastoma, medulloblastoma, meningioma, glioma, mixed glioma, oligodendroglioma, pineal region tumors and pituitary tumors.

4. The method of claim 1, wherein the treatment of the brain tumor in the subject is for the treatment, avoidance or delay of recurrence of a brain tumor.

5. The method of claim 1, wherein the subject is a human with suspected glioma, therapy-naive or previously undergone a cancer treatment, who receives a standard biopsy after cranioanatresis under local or general anaesthesia.

6. The method of claim 1, wherein the subject is a human eligible for tumor removal who receives a standard operation.

7. The method of claim 1, wherein the combination is administered by at least one or more steps of periodic tumor bed irrigation and drainage with a physiological fluid or with isotonic Tris buffer, or a combination thereof, through one or more indwelling catheters.

8. The method of claim 7, wherein the isotonic Tris buffer has a pH of 7.2-9.1.

9. The method of claim 1, wherein the combination is administered by infusion through one or more catheters left inside the tumor, the tumor's resection cavity or biopsy site, with periodical interruptions for drainage and infusion of a physiological isotonic fluid or with isotonic Tris buffer, or a combination thereof.

* * * * *